United States Patent [19]

Ranki et al.

[11] Patent Number: 4,563,419

[45] Date of Patent: * Jan. 7, 1986

[54] DETECTION OF MICROBIAL NUCLEIC ACIDS BY A ONE-STEP SANDWICH HYBRIDIZATION TEST

[75] Inventors: Tuula M. Ranki; Hans E. Soderlund, both of Espoo, Finland

[73] Assignee: Orion Corporation Ltd., Espo, Finland

[*] Notice: The portion of the term of this patent subsequent to Dec. 4, 2001 has been disclaimed.

[21] Appl. No.: 566,532

[22] Filed: Dec. 29, 1983

Related U.S. Application Data

[63] Continuation-in-part of Ser. No. 434,182, Oct. 14, 1982, Pat. No. 4,486,539.

[30] Foreign Application Priority Data

Oct. 16, 1981 [FI] Finland ............................... 813251

[51] Int. Cl.⁴ .................... C12Q 1/68; C12N 15/00
[52] U.S. Cl. ............................................. 435/6; 435/4; 435/5; 435/91; 435/172.3; 435/188; 435/810; 435/935; 436/501; 436/504; 436/804; 436/808; 436/811; 436/823
[58] Field of Search ............... 436/501, 503, 504, 800, 436/804, 808-810, 811, 815, 823, 63, 94; 435/4, 6, 91, 172.1, 259, 317, 810; 935/76-78, 172.3, 5, 243

[56] References Cited

U.S. PATENT DOCUMENTS

| | | | |
|---|---|---|---|
| 4,059,685 | 11/1977 | Johnson | 436/533 |
| 4,139,346 | 2/1979 | Rabbani | 422/56 |
| 4,302,204 | 11/1981 | Wahl et al. | 436/504 |
| 4,358,535 | 11/1982 | Falkow et al. | 435/5 |
| 4,359,535 | 11/1982 | Pieczenik | 435/317 |

FOREIGN PATENT DOCUMENTS

2019408 10/1979 United Kingdom.
2034323 6/1980 United Kingdom.

OTHER PUBLICATIONS

Gillespie, D. et al., Journal of Molecular Biology, vol. 12(3), pp. 829-842, (1965).
Warnaar, S. O. et al., Biochem. Biophy. Research Comm., vol. 24(4), pp. 554-558, (1966).
Grunstein, M. et al., Proc. Natl. Acad. Sci., USA, vol. 77(11), pp. 6851-6855, (11-1980).
Ranki, M. et al., Gene, vol. 21, pp. 77-85, (1983).
Dunn et al., Cell, vol. 12, pp. 23-36, (1977).
Brechot et al., Lancet, pp. 765-767, (Oct. 10, 1981).
Palva et al., Gene, vol. 15, pp. 43-51, (1981).
Owens et al., Science, vol. 213, pp. 670-672, (1981).
Maniatis et al., Cell, vol. 15, pp. 687-701, (1978).
Dunn, A. R. et al., Cell, vol. 15, pp. 23-36, (1978).
Kimmel, A. R. et al., Cell, vol. 16(4), pp. 787-796, (1979).
Long, E. O. et al., Cell, vol. 18(11), pp. 1185-1196, (1979).
Gillis, M. et al., International Journal of Systemic Bacteriology, vol. 30(1), pp. 7-27, (1980).
Manning, J. et al., Biochemistry, vol. 16, pp. 1364-1370, (1977).
Langer, P. R. et al., Proc. Natl. Acad. Sci., USA, vol. 78(11), pp. 6633-6637, (1981).
Bauman, J. C. J. et al., Chromasoma, vol. 84, pp. 1-18, (1981).
Dunn et al., Methods of Enzymology, vol. 65, (7), pp. 468-478, (1980).
Moseley et al., Journal of Infectious Diseases, vol. 142, pp. 892-898, (1980).
Brautigam et al., Journal of Clinical Microbiology, vol. 12, pp. 226-234, (1980).
Grunstein, M. et al., Proc. Nat'l Acad. Sci., vol. 72, (10), pp. 3961-3965, (10-1975).
Brandsma et al., Proc. Natl. Acad. Sci., USA, vol. 77(11), pp. 6851-6855, (11-1980).

Primary Examiner—Thomas G. Wiseman
Assistant Examiner—M. Moskowitz
Attorney, Agent, or Firm—Brumbaugh, Graves, Donohue & Raymond

[57] ABSTRACT

This invention relates to a kit for the detection of microbial nucleic acids and a method for identifying the nucleic acids using a one-step sandwich hybridization technique. The technique requires two complementary nucleic acid reagents for each microbe or group of microbes to be identified.

8 Claims, No Drawings

DETECTION OF MICROBIAL NUCLEIC ACIDS BY A ONE-STEP SANDWICH HYBRIDIZATION TEST

BACKGROUND OF THE INVENTION

This application is a continuation-in-part of prior U.S. application Ser. No. 434,182, filed Oct. 14, 1982, now U.S. Pat. No. 4,486,539.

The present invention relates to a kit for the detection of microbial nucleic acids and a method for identifying said nucleic acids using a one-step sandwich hybridization technique.

In traditional microbial diagnostics the presence of a microbe in a given sample is demonstrated by isolating the microbe in question. After enrichment cultivations, the microbe is identified either on the basis of its biochemical properties or its immunological properties. Both methods of identification require that the microbe in the sample be viable. Such identification can be laborious and time-consuming. Indeed, the detection of certain viruses, requiring sophisticated biochemical purification or tissue culture techniques, can take as long as 4 to 6 weeks.

The purpose of this invention is to provide a diagnostic kit for detecting the nucleic acid of a microbe in a sample with the aid of a sensitive and specific nucleic acid hybridization technique. The nucleic acid may be of two types, deoxyribonucleic acid (DNA) or ribonucleic acid (RNA).

Nucleic acid hybridization is an old and well known method for investigating the identity of nucleic acids. Hybridization is based on complementary base pairing. When single-stranded nucleic acids are incubated in solution, complementary base sequences pair to form double-stranded stable hydrid molecules. The double-stranded hybrid molecules can be separated from the single-stranded molecules by chemical means.

Some methods based on the identification of nucleic acid(s) have already been applied to microbial diagnostics. Enterotoxigenic *Escherichia coli* has been identified from fecal samples by colony hybridization using the gene for toxin production as a probe. Positive hybridization has been demonstrated by autoradiography (see Moseley et al., *Journal of Infectious Diseases*, Vol. 142, pp. 892–898 (1980). Grunstein and Hogness have reported a method for detecting nucleic acids by colony hybridization in *Proc. Natl. Acad. Sci. USA*, Vol. 72, pp. 3961–3965 (1975). Hybridization has also been used as a method to distinguish between Herpes simplex virus type 1 and type 2 after enrichment cultivation (see Brautigam et al., *Journal of Clinical Microbiology*, Vol. 12, pp. 226–234 (1980). In the latter method, the double-stranded hybrid was separated from the single-stranded nucleic acid by affinity chromatography.

Brandsma and Miller have identified DNA from cells infected with Epstein-Barr virus by hybridizing filters containing immobilized Epstein-Barr virus DNA with a radioactive probe, positive hybridation being detected by autoradiography as described in *Proc. Natl. Acad. Sci. USA*, Vol. 77, pp. 6851–6855 (1980).

The present invention is an improvement over the two-step hybridization technique, also called the sandwich hybridization technique, described by Dunn and Hassell in *Cell*, Vol. 12, pp. 23–36 (1977). The sandwich hybridization test described by Dunn et al. is a true two-step hybridization test necessitating two separate hybridization steps. A first hybridization occurs between the nucleic acid affixed onto the solid support and the sample nucleic acid, followed by extensive washing of the solid support. A second hybridization occurs between the washed nucleic acid on the support and a radioactive nucleic acid probe.

The two-step sandwich technique has been used for studying nucleic acids which are inherently single-stranded, that is RNA or single-stranded DNA. If the nucleic acids are double-stranded or double-stranded having been rendered single-stranded, the presence of complementary strands results in the annealing of the nucleic acids, thereby at least partially preventing the hybridization of the labelled probe in the second hybridization step. The present invention avoids the drawbacks of the two-step sandwich hybridization technique by employing a competitive one-step sandwich hybridization technique. Because of this fact the one-step sandwich hybridization technique is more sensitive than the two-step sandwich hybridization technique. Furthermore, it is more rapid to perform and requires less hybridization mixture and washing solution. Consequently the one-step sandwich hybridization technique is more suitable for routine diagnostics.

SUMMARY OF THE INVENTION

A highly sensitive one-step sandwich hybridization technique has been developed for the detection of nucleic acids. A given microbe or microbial group can be detected from a crude sample by its double-stranded or single-stranded nucleic acids. One-step sandwich hybridization requires the simultaneous addition of two purified nucleic acid reagents for each microbe or group of microbes to be identified. The reagents are two distinct single-stranded nucleic acid fragments isolated from the genome of the microbe to be identified, which fragments have no extensive sequence homology in common (i.e. do not cross-hybridize) but preferably are situated close together in the genome and are produced by using the established recombinant DNA techniques. One of the nucleic acid fragments is affixed onto a solid carrier, preferably a nitrocellulose filter, and the other fragment, also in single-stranded form, is labelled with a suitable label. After the sample nucleic acids to be identified are rendered single-stranded, they are contacted with single-stranded nucleic acid reagents. Annealing of complementary base pairs results in the formation of double-stranded hybrids, i.e. nucleic acid sample/labelled reagent and nucleic acid sample/reagent affixed to solid carrier.

The invention encompasses nucleic acid fragments prepared by conventional vectors, hosts, ligases, transcriptases and cultivation and separation procedures. Typical vectors are plasmids, cosmids and bacteriophages, such as the plasmids pBR322, pUB110, λ-phage and bacteriophage M13 mp 7. It is particularly useful to employ two separate vectors, one for the solid carrier affixed nucleic acid reagent and another for the labelled nucleic acid reagent in order to avoid the occurrence of residual vector sequences, thereby minimizing hybridization background. It is preferred to produce the fragments by using restriction enzymes such as BamHI, Pst I, EcoRI and XhoI. Representative nucleic acid fragments contain a range of base pairs from at least 10 base pairs to several thousand base pairs. Nucleic acid fragments of 300 to 4000 base pairs are preferred. The length of the fragments are relatively unimportant so long as the fragments can cross-hybridize with the sample nucleic acid to form stable hybrids.

Once nucleic acid fragments have been prepared, nucleic acid fragments are affixed to a solid carrier. Suitable solid carriers are nitrocellulose sheets or conventional modified paper, such as nitrobenzoyloxymethyl paper or diazobenzyloxymethyl paper as described by Wahl et al. in U.S. Pat. No. 4,302,204 or aminobenzoyloxymethyl paper described by Rabbini et al. in U.S. Pat. No. 4,139,346. Nylon membranes and modified nitrocellulose might be used as well. The only limitations on the solid carrier is that it must be capable of affixing nucleic acids in single-stranded form such that the single-stranded nucleic acids are available to hybridize with complementary nucleic acids and that the carrier can be easily removed from the hybridization mixture.

Nucleic acid fragments are labelled with radioisotopes, such as $^{125}$I and $^{32}$P, fluorochromes, chromogens and enzymes. Lanthanide chelates detected by delayed fluorescence and described in U.S. Pat. No. 4,374,120 and U.S. Pat. No. 4,374,120 are suitable labels, as well as the biotin-avidine labels described by J. J. Leary, et al. in P.N.A.S., Vol. 80, pp. 4045–4049 (1983). When a radioactive label is used, it is preferred to use one with specific activity of $10^7$ to $10^9$ cpm/μg DNA.

The kit described in this invention can in principle be used for the identification of DNA- or RNA-containing organisms, such as viruses, bacteria, fungi and yeasts. The kit has the specific advantage of simultaneously detecting specific bacteria anf viruses from a mixed sample regardless of whether the microbes contain DNA or RNA. By suitable combination of reagents it is possible to develop kits such that each microbe to be identified has its own specific solid carrier and labelled nucleic acid reagent. All the filters included in the reagent combination can be added to the sample simultaneously, along with the labelled nucleic acid reagents. When hybridization has taken place, the solid carriers are washed and their labelling is measured. The technique is highly sensitive.

Kits of this invention can be used, e.g. in medical microbiology, veterinary microbiology and food hygiene investigations and microbial diagnostics of plant diseases. Suitable sample materials are animal and plant tissue homogenates, blood, feces and nasal and urethral mucous. It can be estimated that the kit is sufficiently sensitive to detect microbe levels normally present in clinical samples. Preliminary enrichment of the microbe present in the sample by cultivation is of course possible before the identification test and in some cases would be essential. The kit is also suitable for the investigation of samples from which the microbe can no longer be cultivated but which contain considerably amounts of microbial debris (e.g. after the commencement of antibiotic treatment), or when cultivation of the microbe is particularly laborious and difficult (e.g. anaerobic bacteria, which are present in large numbers in suppurative samples in the case of infections caused by anaerobes).

Representative kits of the invention can be used to detect the nucleic acid(s) present in the following:
Respiratory infections:
(a) Bacteria: β-hemolytic streptococci (group A), *Hemophilus influenzae*, pneumococci, *Mycoplasma pneumoniae*, mycobacteria
(b) Viruses: influenza A, influenza B, parainfluenza (types 1, 2 and 3), respiratory syncytial virus, adenoviruses, coronaviruses, rhinoviruses
Diarrhoeas:
(a) Bacteria: salmonellae, shigellae, *Yersinia enterocolitica*, enterotoxigenic, *E. coli*, *Clostridium difficile*, campylobacter
(b) Viruses: rotaviruses, parvoviruses, adenoviruses, enteroviruses
Venereal diseases:
(a) Bacteria: *Neisseria gonorrhoeae*, *Treponema pallidum*, *Chlamydia trachomatis*
(b) Viruses: Herpes simplex virus
(c) Yeasts: *Candida albicans*
(d) Protozoa: *Trichomonas vaginalis*
Sepsis:
(a) Bacteria: β-hemolytic streptococci (group A), pneumocci, enterobacteria
Food hygiene:
(a) Bacteria: salmonellae and *Clostridium perfringens*.

The specificity of the diagnostic kit can be limited to a defined microbial group (e.g. salmonella bacteria) or broadened to a wider microbial group (e.g. enterobacteriaceae) by selecting particular nucleic acid fragments.

DESCRIPTION OF THE PREFERRED EMBODIMENTS

The nucleic acid reagents required in the one-step sandwich hybridization technique are produced by recombinant DNA technology. The recombinant plasmids used as nucleic acid reagents in the one-step hybridization technique of this invention are cloned into the host *Escherichia coli* K12 HB 101. Deposits of recombinant plasmids have been made in the Deutsche Sammlung von Mikroorganismen (DSM), Grisebachstrasse 8, D-3400 Goettingen, Germany (Federal Republic) and in the National Public Health Institute (KTL), Mannerheimintie 166, Helsinki, Finland. The deposit numbers are as follows:

| Plasmid | DSM | KTL |
| --- | --- | --- |
| pKTH1201 | DSM 2823 | EH 231 (KTL) |
| pKTH1201 | DSM 2824 | EH 230 (KTL) |
| pKTH45 | DSM 2821 | EH 254 (KTL) |
| pKTH312 | DSM 2822 | EH 232 (KTL) |

The recombinant phage mKTH 1207 was deposited at DSM and KTL under deposit numbers, DSM 2828 and EH 256 (KTL), respectively. The following describes the reagent production and test procedures for Example 1.

Reagents

Adenovirus type 2 (Ad$_2$) (ATCC VR-846) was obtained from KTL, the National Public Health Laboratory located in Helsinki, Finland. Ad$_2$ was cultivated and purified and its DNA was isolated in accordance with the procedure set forth by Petterson and Sambrook in the *Journal of Molecular Biology*, Vol. 73, pp. 125–130 (1973). The DNA was digested with BamHI-restriction enzyme obtained from Bethesda Research Laboratories (BRL), which enzyme cuts the DNA into four reproducible fragments. Two of these fragments were inserted into the BamHI-site of the vector plasmid pBR322 (BRL) with the aid of T4-ligase (BRL). The fragments were not separated before ligation, but the insert was in each case identified only after cloning. The bacterial host, *E. coli* HB101 (K12) gal$^-$, pro$^-$, leu$^-$, hrs$^-$, hrm$^-$, recA, str$^R$, F$^-$, obtained from KTL, was transformed with the plasmid DNA composed of recombinant plasmids, i.e. molecules which had accepted fragments of the adenovirus DNA, by the procedure set forth in Cohen et al. in *Proc. Natl. Acad. Sci. USA*, Vol. 69, pp. 2110–2114 (1972).

Bacterial clones which contained recombinant plasmids were chosen. Ampicillin and tetracycline resistance were transferred to the bacterium by the pBR322-plasmid (Bolivar et al., *Gene*, Vol. 2, pp. 95–113 (1977)). Bacteria containing the recombinant plasmid were sensitive to tetracycline, because the BamHI-restriction site was within the tetracycline gene and the foreign DNA inserted into this region destroyed the gene. The insert of the plasmid was characterized after plasmid enrichment by determining the size of the restriction fragments after BamHI digestion using agarose gel electrophoresis. Adjacent BamHI D- and C-fragments of the $Ad_2$-DNA were chosen as reagents (Soderlund et al., *Cell*, Vol. 7, pp. 585–593 (1976)).

The preferred recombinant plasmids, $Ad_2C$-pBR322 or pKTH1201, assigned deposit No. DSM 2823 at the DSM and deposit No. EH231 at the KTL, and $Ad_2D$-pBR322 or pKTH 1202, assigned deposit No. DSM 2824 at the DSM and deposit No. EH230 at the KTL, were cultivated and purified by conventional methods, see for example Clewell and Helinski in *Proc. Natl. Acad. Sci. USA*, Vol. 62, pp. 1159–1166 (1969).

The recombinant plasmid $Ad_2D$-pBR322 was used as the filter reagent. It was not necessary for purposes of the invention to remove the plasmid sequences. However, for the radioactive labelling, the nucleic acid was separated from pBR322-DNA after BamHI-digestion with the aid of agarose gel electrophoresis. The C-fragment was isolated from LGT-agarose (Marine Colloids, Inc.) by phenol extraction or electro-elution (Wieslander, *Anal. Biochem.*, Vol. 98, pp. 305–309 (1979) and concentrated by ethanol precipitation.

It was particularly expedient to subclone the nucleic acid fragment chosen for labelling in a separate vector, in order to avoid the hybridization background resulting from the direct hybridization with the filter of the residual plasmid sequences, contaminating the labelled nucleic acid reagent. The single-stranded DNA-phage M13 mp7 (BRL) could be used as an optimal vector (Messing et al., *Nucleic Acids Research*, Vol. 9, pp. 309–323 (1981)).

Attachment of DNA to the filter

The recombinant plasmid $Ad_2D$-pBR322 was denatured to a single-stranded form and nicked randomly at several sites by treatment with 0.2N NaOH for 5 minutes at 100° C., whereafter the DNA was chilled and, immediately prior to transference to the filter, neutralized and pipetted to the transfer solution, 4×SSC medium on ice (SSC=0.15M NaCl, 0.015M Na-citrate). The filters (Schleicher and Schull BA85 nitrocellulose) were thoroughly wetted in 4×SSC solution for about 2 hours before the application of DNA. The DNA was attached to the filter in a dilute solution (0.5–1.0 μg/ml) by sucking the solution through the filter in a weak vacuum. The filter was capable of absorbing DNA up to about 180 μg/cm$^2$ (see Kafatos et al., *Nucleic Acids Research*, Vol. 7, pp. 1541–1552 (1979)). DNA concentrations of between 0.5 μg DNA/2.5 cm diameter of filter and 1.0 μg DNA/0.7 cm diameter of filter were used. After DNA filtration the filters were washed in 4×SSC, dried at room temperature and finally baked in a vacuum oven at 80° C. for 2 hours. Since the DNA on the filters was stable, the filters were stored for long periods at room temperature (Southern, *Journal of Molecular Biology*, Vol. 98, pp. 503–517 (1975)).

Labelling of the radioactive nucleic acid fragment

The radioactive label used was the $^{125}$I-isotope, which was quantitated by gamma counters. Since the half-life of the isotope is 60 days, the utilization period of $^{125}$I-labelled reagents is about 4 months.

"Nick-translation" labelling

This method displaces one of the nucleotides in the nucleic acid with a radioactive one, whereby upon replication the whole DNA molecule is labelled. This was carried out according to the method published by Rigby et al. in the *Journal of Molecular Biology*, Vol. 113, pp. 237–251 (1977). The DNA was labelled in a solution containing a $^{125}$I-labelled deoxynucleoside triphosphate such as $^{125}$I-dCTP (Radiochemical Centre, Amersham: >1500 Ci/mmol) as substrate. Under optimal conditions a specific activity of $10^9$ cpm/μg DNA was obtained. The labelled DNA was purified from nucleotides remaining in the reaction mixture by simple gel filtration, e.g. using BioGel P30 (BioRad).

Other labelling methods

The single-stranded nucleic acid reagent produced in M13 mp7-phage was labelled by chemical iodination, in which the reactive $^{125}$I was added covalently to the nucleic acid (see Commerford, *Biochemistry*, Vol. 10, pp. 1993–2000 (1971) and Orosz et al., *Biochemistry*, Vol. 13, pp. 5467–5473 (1974)). Alternatively, the nucleic acid was made radioactive by end-labelling with radioactive nucleotides by the terminal transferase (see Roychoudhury et al., *Methods of Enzymology*, Vol. 65, pp. 43–62 (1980)).

Reagents for microorganisms containing RNA

The reagent preparation described above has related to microbes whose genetic material is in the form of DNA. In the case of RNA viruses, the cloning of genome fragments took place after a DNA copy (cDNA) of the virus RNA was made with the aid of reverse transcriptase, followed by DNA-polymerase, to copy the second DNA strand, therafter the DNA was cloned as described above (see Salser, *Genetic Engineering*, Ed. Chakrabarty, CRC Press, pp. 53–81 (1979)).

The most suitable cloning method is chosen depending on the microbe used. The hosts as well as the vectors vary. For example, vector possibilities include the λ-phage, other plasmids, cosmids, cloning e.g. in bacterial hosts such as *Bacillus subtilis* and *Escherichia coli* (Recombinant DNA, *Benchmark Papers in Microbiology*, Vol. 15, Eds. Denniston and Enqvist, Dowden, Hutchinson and Ross, Inc. (1981) and Ish-Horowicz et al., *Nucleic Acids Research*, Vol. 9, pp. 2989–2998 (1981)).

Performance of the test

Sample treatment

The nucleic acid to be identified is released from a microbe or from infected cells by mechanical or chemical (lysozyme and EDTA) means. Virus genomes are isolated, for example, by treating the viral sample with 1% sodium dodecylsulphate (SDS). The proteins which protect the viral genome are removed by conventional procedures, for example, by proteinase K treatment (1 mg/ml, 37° C., 60 minutes). If the sample contained larged quantities of viscous high molecular weight cellular DNA, the cellular DNA is sheared by sonication or by passing it through a fine needle.

Hybridization

The nucleic acids of the sample are rendered single-stranded by boiling for about 5 minutes and quick cooling at 0° C. A hybridization mixture is added to the denatured nucleic acid sample and this mixture is pipetted onto a solid carrier, e.g. a nitrocellulose filter, in the hybridization vessel. There are many hybridization mixtures which are suitable for one-step sandwich hybridization; see the hybridization mixtures described by Denhardt in *Biochem. Biophys. Research Communications,* Vol. 23, pp. 641–646 (1966) and by Wahl et al. in U.S. Pat. No. 4,302,204. A representative hybridization mixture is 50% formamide (deionized, stored at −20° C.) in a 4×SSC with Denhardt solution, containing 1% SDS and 0.5 mg/ml DNA (salmon sperm or calf thymus). The single-stranded nucleic acid hybridizes with a combination of purified nucleic acid reagents, one of which is labelled and one of which is affixed to a solid carrier. Hybridization occurs in a single step and typically at a temperature of 37° C. over a period of 16–20 hours.

Washing

After hybridization has taken place, the solid carrier is removed from the hybridization vessel and carefully washed by a dilute SSC solution, preferably 0.1×SSC. It is essential that the washing solution contains SDS to inhibit any nuclease activity of the sample.

Measuring

The amount of radioactive label remaining on the washed carrier is measured by conventional methods, e.g. a scintillation or a gamma-counter. An alternative method for measuring radioactivity is autoradiography. If fluorescent or enzymatic labels are employed, they are measured by numerous conventional methods.

Background is measured by the use of suitable controls, i.e. a solid carrier containing no nucleic acid at all, a solid carrier containing thymus nucleic acid or some other indifferent nucleic acid, and a solid carrier containing all relevant reagents but no sample nucleic acids.

The invention is illustrated by the following examples:

EXAMPLE 1

The sandwich hybridization method in accordance with the invention detected viral DNA in a solution as well as viral DNA in infected cells.

HeLa cells were infected with type 2 adenovirus. The cells were then disrupted by treatment with 1% SDS, followed by digestion with 1 mg/ml proteinase K enzyme (Sigma) for 30 minutes at 37° C. Before denaturation the sample was passed through a fine needle. For the details concerning the filters, nucleic acid reagents and hybridization, refer to the text of Table 1.

TABLE 1

|  | Filters (cpm) | | |
| --- | --- | --- | --- |
|  | Adeno(1) | Calf thymus(2) | Blank(3) |
| Samples |  |  |  |
| Adenovirus type 2 DNA (BRL) (500 ng) | 9000 | 49 | — |
| HeLa cells (6 × 10⁵) infected with adenovirus | 8200 | — | — |

TABLE 1-continued

Filters:
(1) Ad₂D-pBR322-plasmid, 2 μg
(2) Calf thymus DNA 1 μg (Boehringer Mannheim)
(3) Blank (no DNA)
Labelled nucleic acid reagent:
Ad₂-BamHI C-fragment, purified, specific activity 90 × 10⁶ cpm/μg (200000 cpm ¹²⁵I/reaction)
Hybridization:
50% formamide, 4 × SSC, Denhardt solution, containing 0.5 mg/ml salmon sperm DNA and 1% SDS for 16 hours at 37° C.
Washing:
0.1 × SSC for 40 minutes at room temperature Adenovirus DNA fragments hybridized to adenovirus type 2 DNA and to adenovirus DNA from HeLa cells infected with adenovirus as shown in the above Table 1. The hybridization background radiation was measured in a tube containing only the filter and the labelled nucleic acid reagent, without the sample. The background radiation came from the pBR322 sequences which occurred in the labelled nucleic acid reagent. These sequences hybridized directly with the filter without the mediation of the sample. The filters containing calf thymus and no DNA were used in the test as controls, indicating on the one hand the specificity of hybridization and on the other the level of the nonspecific background radiation arising, e.g. from insufficient washing. The values appearing in Table 1 were corrected by subtraction of the reagent background, obtained by carrying out a similar hybridization but without sample. The background due to the reagents was subtracted from the cpm-values hybridized to the filters.

EXAMPLE 2

The sandwich hybridization method in accordance with the invention detected viral RNA in solution and in infected cells.

The model single-stranded RNA-virus used was the Semliki Forest virus, prototype strain, obtained from the London School of Hygiene and Tropical Medicine. Using the virus genome as a template cDNA was produced, which was cloned into the pstI site of pBR322 plasmid as described by Garoff et al. in *Proc. Natl. Acad. Sci. USA,* Vol. 77, pp. 6376–6380 (1980). The recombinant plasmid, called pKTH312, was deposited at DSM under the deposit No. DSM 2822 and at KTL under deposit No. EH 232. The insert of this plasmid, originating from the virus genome, is about 1400 nucleotides long, and is derived from the structural protein area, approximately from nucleotide 200 to nucleotide 1600. The whole recombinant plasmid pKTH312 was linearized with EcoRI restriction enzyme (BRL) since the sequence originating from the Semliki Forest virus did not contain recognition sites for the EcoRI-enzyme. The linearized plasmid was cut into two fragments using XhoI-enzyme (BRL). The restriction site of the latter was located within the Semliki Forest virus sequence. The larger EcoRI-XhoI-fragment A (about 3900 base pairs) was attached to the filter and the smaller fragment B (about 1850 base pairs) was labelled with ¹²⁵I using the nick-translation technique.

BHK-21 cells were infected with Semliki Forest virus. Semliki Forest virus (30 μg) was disrupted with SDS before the test. The infected cells were handled as described in Table 1.

TABLE 2

| | Filters (cpm) | | |
|---|---|---|---|
| | Semliki Forest virus(1) | Calf thymus(2) | Blank(3) |
| Samples | | | |
| Semliki Forest virus 30 μg | 3340 | — | 33 |
| Cells infected with Semliki Forest virus (5 × 10$^5$) | 2698 | 8 | 10 |
| Non-infected cells | 10 | 5 | 8 |

Filters:
(1) EcoRI-XhoI-fragment A (1.2 μg) of the pKTH312 plasmid
(2) Calf thymus DNA 1 μg
(3) Blank (no DNA)
Labelled nucleic acid reagents:
EcoRI-XhoI-fragment B of the plasmid pKTH312, specific activity 90 × 10$^6$ cpm/μg DNA (200,000 cpm $^{125}$I/reaction).
Hybridization:
See text of Table 1.
Washing:
See text of Table 1.

Semliki Forest virus specific fragments hybridized to Semliki Forest virus RNA and to Semliki Forest virus RNA from the BHK-21 cells infected with Semliki Forest virus as shown in the above Table 2. The values given in the table have been corrected for reagent background, obtained from a similar hybridization without sample.

EXAMPLE 3

Viral messenger RNA was detected in solution and in infected cells with the aid of the sandwich hybridization method.

The filter hybridization reagents were produced from SV40-virus DNA (BRL) by cutting the DNA into two parts using PstI-enzyme (Boehringer Mannheim) as described by Lebowitz and Weissman in *Current Topics in Microbiol. Immunol.*, Vol. 87, pp. 43–172 and the fragments were isolated and purified by agarose gel electrophoresis. Fragment A (4000 base pairs) was radioactively labelled with $^{125}$I by nick-translation and fragment B (1220 base pairs) was attached to the filter.

The DNA fragments were chosen so that each contained areas coding for both early and late messengers. Thus fragment B contained about 700 bases from the structural protein gene VP1 and over 600 bases from the gene for early messengers. Because the DNA of SV40 virus is in itself a covalently closed ring, it cannot be detected by the test before linearization. Therefore, when infected cells were used as the sample it was possible to test how well the method was adaptable to the detection of RNA copies of the viral genome. As can be seen from the results in Table 3, the test was excellently suited to the investigation of infected cells. The table also demonstrated that the same reagents could be used to investigate both the viral DNA and mRNA made from it.

SV40-virus DNA (BRL) was linearized with EcoRI restriction enzyme (BRL). CV1-cells (Biomedical Centre, Upsala University) were infected with SV40-virus (obtained from Chou and Martini, NIH, Bethesda) and the cells were harvested 40 hours after infection. Treatment of the sample was as described in Table 1.

TABLE 3

| | Filters (cpm) | | |
|---|---|---|---|
| | SV40(1) | Calf thymus(2) | Blank(3) |
| Samples | | | |
| Test 1 | | | |
| SV40 viral DNA (50 ng) (linearized) | 20061 | 159 | 104 |
| No sample | — | — | — |
| Test 2 | | | |
| CV1-cells infected with SV40-virus 40 hours after infection (10$^6$ cells) | 30814 | 294 | 580 |
| Non-infected cells | — | — | — |

Filters:
(1) The shorter fragment PstI B (0.2 μg) of the circular SV40-virus DNA digested with PstI-restriction enzyme
(2) Calf thymus DNA 1 μg
(3) Blank (no DNA)
Labelled nucleic acid reagent:
The longer PstI A-fragment of the SV40-virus DNA, specific activity 28 × 10$^6$ cpm/μg DNA (200,000 cpm $^{125}$I/reaction)
Hybridization:
See text of Table 1. The time for the hybridization was 40 hours.
Washing:
See text of Table 1.

SV40 fragments hybridized to SV40 viral DNA and to viral nucleic acids from CV1-cells infected with SV40 virus as shown in Table 3. The values presented in the table have been corrected for reagent background, obtained from a similar hybridization carried out without sample.

EXAMPLE 4

*Bacillus amyloliquefaciens* was detected by sandwich hybridization.

The reagents were fragments of the α-amylase gene of *B. amyloliquefaciens* E18 (Technical Research Centre of Finland, VTT), which were isolated for the purpose of this test from the recombinant plasmid pKTH10 (see Palva et al., *Gene*, Vol. 15, pp. 43–51 (1981)) by treatment with restriction enzyme and subsequent agarose gel electrophoresis. The fragments used for this test were the ClaI-EcoRI fragment (460 base pairs) (ClaI Boehringer Mannheim) and the EcoRI-BamHI fragment (1500 base pairs). The EcoRI-BamHI fragment was attached to the filter and the ClaI-EcoRI fragment was labelled with $^{125}$I by nick-translation.

Bacterial samples were treated with lysozyme (67 μg/ml) for 30 minutes at 37° C. and 5 mM EDTA was added to the *E. coli* samples. SDS was added to all the samples (final concentration 2%) and the samples were passed twice through a fine needle to reduce their viscosity before being denatured by boiling as described in the text relating to handling of samples.

As can be seen from Table 4, the *B. amyloliquefaciens* was identifiable by sandwich hybridization on the basis of the single α-amylase gene. *E. coli* gave a result in this test which was indistinguishable from the background.

TABLE 4

| | Filters (cpm) | | |
|---|---|---|---|
| | α-amylase(1) | Calf thymus(2) | Blank(3) |
| Samples | | | |
| pKTH10-plasmid-DNA (linearized) 1 μg | 5773 | 47 | — |
| No sample | — | — | — |
| *E. coli* HB101 (10$^9$) | — | — | — |
| *Bacillus amyloliquefaciens* (3 × 10$^9$) | 3377 | — | — |

TABLE 4-continued

| | | | |
|---|---|---|---|
| *Bacillus amylolique-faciens* ($10^9$) | 2871 | — | — |

Filters:
(1) The EcoRI-BamHI fragment of the α-amylase gene from plasmid pKTH10, 0.35 μg
(2) Calf thymus DNA, 1 μg
(3) Blank (no DNA)

Labelled nucleic acid reagent:
The ClaI-EcoRI fragment of the α-amylase gene from plasmid pKTH10, specific activity $35 \times 10^6$ cpm/μg (200,000 cpm $^{125}$I/reaction)

Hybridization:
See text of Table 1.
Washing:
See text of Table 1.

The values appearing in the table have been corrected for reagent background, obtained from a similar hybridization without sample.

EXAMPLE 5

A reagent combination kit in accordance with the invention detected specific viral and bacterial nucleic acids in a given sample.

The samples investigated in this test were cells infected by three viruses (adenovirus, SV40 virus and Herpex simplex virus) and a sample containing *Bacillus amyloliquefaciens* bacteria. As shown in Table 5, the following reagents were all simultaneously added to each sample: 5 filters, each containing one type of DNA from SV40 virus, adenovirus, *Bacillus amyloliquefaciens*, α-amylase gene and calf thymus, a filter containing no DNA at all, and 200,000 cpm of each of the following labelled nucleic acid reagents: SV40 virus, adenovirus and α-amylase gene DNA reagent.

Cell samples infected with SV40 virus and adenovirus have been described in Tables 3 and 1, respectively. $10^6$ Vero cells were infected with Herpes simplex virus type 1. The cells were harvested 20 hours post infection when cytopathic effect was observed.

TABLE 5

| | Filters (cpm) | | | | |
|---|---|---|---|---|---|
| | SV40 (1) | Adeno (2) | α-amylase (3) | Calf thymus(4) | Blank (5) |
| Samples | | | | | |
| Cells infected with SV40 virus ($10^6$) | 18390 | 2 | 13 | 22 | 31 |
| Cells infected with adenovirus type 2 ($6 \times 10^5$) | — | 8750 | 5 | 13 | — |
| Cells infected with Herpex simplex virus ($10^6$) | — | — | — | 5 | 13 |
| *Bacillus amylolique-faciens* ($10^9$) | 15 | 8 | 6500 | 16 | 5 |
| Non-infected cells | — | — | — | — | — |

Filters:
(1) See Table 3.
(2) See Table 1.
(3) See Table 4.
(4) Calf thymus DNA, 1 μg
(5) Blank (no DNA)

Labelled nucleic acid reagents:
SV40 virus as in Table 3
Adenovirus as in Table 1
α-amylase gene as in Table 4
Hybridization:

TABLE 5-continued

See text of Table 1.
Washing:
See text of Table 1.

Table 5 has shown that it is possible, without division or dilution of the sample, to investigate simultaneously a series of microbes by adding a suitable reagent combination to the sample. The filters were recognized by a sign such as a mark or tag, which identified the sequence it contained.

The values in the table were corrected for reagent background, obtained by carrying out a similar hybridization without sample.

EXAMPLE 6

DNA was detected in purified *E. coli* DNA samples and in disrupted *E. coli* cells by the sandwich hybridization method in accordance with the invention.

DNA from *E. coli* K12 HB101 was isolated according to the method described by Marmur in the *Journal Molecular Biology*, Vol. 3, pp. 208-218 (1961). The DNA was denatured by treating with 7 mM NaOH at 100° C. for 5 min.

The *E. Coli* cells were treated with the following solutions: 500 μg/ml lysozyme, 70 mM EDTA at 37° C. for 30 min. and 0.25% SDS at +65° C. The free DNA was denatured by boiling in 14 mM NaOH at +100° C. for 5 min.

The reagents were prepared from the outer membrane protein A-gene of *Escherichia coli*, called the ompA-gene. The hybrid plasmids pKTH40 and pKTH45, used as the starting materials, were prepared from the pTU100 plasmid described by Henning et al. in *Proc. Natl. Acad. Sci. USA*, Vol. 76, pp. 4360-4364 (1979).

The plasmid pKTH45 was deposited under deposit No. DSM 2821 at DSM and under deposit No. EH254 at the KTL in Helsinki, Finland. This plasmid was attached to the filter. It contained 740 base pairs from the 5'-terminal end of the ompA-gene inserted into the pBR322-plasmid.

The plasmid pKTH40 contained 300 base pairs from the 3'-terminal end of the ompA-gene and the immediately following 1400 base pairs from the genome of *E. coli*. The pKTH40 plasmid was cleaved with the BamHI restriction enzyme to retrieve the DNA fragment of *E. coli*, which contained the 1700 base pairs mentioned above. This fragment was transferred to the single-stranded bacteriophage M13mp7 in accordance with the conventional methods, see for example Messing et al. in *Nucleic Acids Research*, Vol. 9, pp. 309-321 (1981), Heidecker et al. in *Gene*, Vol. 10, pp. 69-73 (1980) and Gardner et al. in *Nucleic Acids Research*, Vol. 9, pp. 2871-2888 (1981).

The recombination-phage mKTH1207 was deposited under deposit No. DSM 2828 at DSM and under deposit No. EH256 at the KTL. This recombination-phage was labelled with an $^{125}$I-isotope as described under the heading "Other labelling methods" and was used as a probe in the sandwich hybridization method.

As shown in Table 6, the *E. coli* was identifiable by sandwich hybridization on the basis of the outer membrane protein A-gene.

TABLE 6

| | Filters (cpm) | | |
|---|---|---|---|
| | ompA(1) | Calf thymus(2) | Blank(3) |

TABLE 6-continued

| Samples | | | |
|---|---|---|---|
| *E. coli* K12 HB101 DNA (a) $2 \times 10^7$ | 282 | — | — |
| *E. coli* K12 HB101 DNA (a) $2 \times 10^8$ | 2206 | — | — |
| *E. coli* K12 HB101 cells (b) $2 \times 10^7$ | 1113 | — | — |
| *E. coli* K12 HB101 cells (b) $2 \times 10^8$ | 2327 | 12 | 5 |

(a) number of DNA-molecules
(b) number of cells

Filters:
(1) pKTH45 plasmid 1.088 μg ($2 \times 10^{11}$ molecules)
(2) Calf thymus DNA 1.088 μg
(3) Blank (no DNA)

Labelled nucleic acid reagent:
mKTH1207, specific activity $8 \times 10^7$ cpm/μg DNA (200,000 cpm/reaction)

Hybridization:
$4 \times$ SSC, $1 \times$ Denhardt solution without BSA (bovine serum albumin), containing 200 μg/ml Herring sperm DNA and 0.25% SDS, at $+65°$ C. for 17.5 hours Washing:
See text of Table 1.

The values presented in the table have been corrected for reagent background, obtained from a similar hybridization without sample.

EXAMPLE 7

Two studies (A and B) were conducted to compare one-step sandwich hybridization with two-step sandwich hybridization.

The reagents used were adenospecific filters containing 0.4 μg DNA, control filters containing calf thymus DNA or no DNA, adenospecific probes having a specific activity of $10^8$ cpm/μg, (200,000 cpm/reaction), and adenovirus type 2 DNA (0.2 ng, 0.5 ng, 1 ng and 2 ng) to be used as the sample DNA. The hybridization mixture contained $6 \times$ SSC, 0.02% Ficoll and 0.02% polyvinylpyrrolidone, 0.2% SDS and 200 μg/ml of denatured herring sperm DNA. The hybridization was carried out at a temperature of $65°$ C. for a period of 20 hours, whereupon the filters were washed with a solution ($50°$ C.) of $0.1 \times$ SSC containing 0.2% SDS for a period of 2 hours. The radioactivity was quantitated by a Wallac Compugamma counter.

In the Study A, the one-step sandwich hybridization was carried out under the conditions described above by simultaneously incubating the sample DNA with the adenospecific filters and with the probe DNA. In the Study B, the first-step of the two-step sandwich hybridization was carried out by incubating the sample DNA with the adenospecific filters. After the initial 20 hour incubation period and subsequent washing of the filters, the second-step of the two-step sandwich hybridization was carried out by incubating the washed filters with the probe DNA. After a 20 hour incubation period, the filters were washed and counted.

The results of Studies A and B are set forth as follows:

| Sample | cpm incorporated | |
|---|---|---|
| Adeno-DNA (ng) | A | B |
| 0.2 | 54 | 2 |
| 0.5 | 123 | 33 |
| 1 | 265 | 138 |
| 2 | 438 | 310 |

The background reading, that is the radioactivity on the adenospecific filter in a reaction without sample DNA, was 70 cpm. This background reading was substracted from the above values. Values above 50 cpm were positive indicating the presence of adenoviral DNA in the sample.

The sensitivity of Study A (one-step sandwich hybridization) is 0.2 ng, whereas the sensitivity of Study B (two-step sandwich hybridization) is 0.6 ng. In other words, the one-step sandwich hybridization reaction is about three times as sensitive as the two-step sandwich hybridization reaction. The time needed to carry out the one-step sandwich hybridization reaction was a period of 20 hours for hybridization and 2 hours for washing while the time needed to carry out the two-step sandwich hybridization reaction was a period of 20 hours for the first hybridization and 2 hours for washing plus the additional time needed for the second hybridization, that is approximately 20 hours for the second hybridization and 2 hours for washing. This translates into approximately 24 hours additional time. Thus, one-step sandwich hybridization is about two times as fast as the two-step sandwich hybridization. The quantities of reagents, hybridization mixtures and washing solutions were reduced by one-half in the one-step sandwich hybridization reaction.

We claim:

1. A method for identifying microbial nucleic acids by a one-step sandwich hybridization test, said method comprising the steps of:
   (a) rendering the microbial nucleic acids in the sample to be identified single-stranded;
   (b) allowing said microbial single-stranded nucleic acids of the sample to hybridize simultaneously with two purified nucleic acid reagents, both having been isolated from the genome of a known microbe, wherein the first nucleic acid reagent comprises a single-stranded fragment of nucleic acid, having a nucleotide sequence of at least 10 bases and being affixed to a solid carrier, and wherein the second nucleic acid reagent comprises a single-stranded fragment of nucleic acid, having a nucleotide sequence of at least 10 bases and being labelled with a suitable label such that hybridized microbial nucleic acids can be detected, said first and second nucleic acid reagents being capable of base pairing with complementary sequences of the sample nucleic acid to be identified, provided that the second nucleic acid reagent does not hybridize with the first nucleic acid reagent;
   (c) washing said solid carrier to substantially remove said label which is not incorporated into the hybrid formed by the base pairing of the second nucleic acid reagent and the nucleic acids to be identified; and
   (d) measuring said label on the washed solid carrier, whereby determining whether the sample contains the nucleic acid to be identified.

2. The method of claim 1, wherein the solid carrier is selected from the group consisting of a nitrocellulose sheet, nylon membrane, modified paper and modified nitrocellulose sheet.

3. A kit for the detection of one or more microbial nucleic acid sequences with a one-step sandwich hybridization test, the kit comprising in packaged combination a container of one pair of nucleic acid reagents for each nucleic acid sequence to be identified wherein:

(a) a first microbial nucleic acid reagent for a given nucleic acid to be identified comprises a single-stranded fragment of nucleic acid, having a nucleotide sequence of at least 10 bases and being affixed to a solid carrier, wherein said first nucleic acid reagent base pairs with a complementary sequence of the given nucleic acid to be identified; and (b) a second microbial nucleic acid reagent for a given nucleic acid to be identified comprises a single-stranded fragment of nucleic acid, having a nucleotide sequence of at least 10 bases and being labeled with a suitable label such that hybridized microbial nucleic acids can be detected, wherein said second nucleic acid reagent base pairs with a complementary sequence of the given nucleic acid to be identified, such that the second nucleic acid reagent does not hybridize with the first nucleic acid reagent.

4. The kit of claim 3, wherein the solid carrier is selected from the group consisting of a nitrocellulose sheet, nylon membrane, modified paper and modified nitrocellulose sheet.

5. The method of claim 1, wherein the label is selected from the group consisting of radioisotopes, fluorochromes, chromogens and enzymes.

6. The kit of claim 3, wherein the label is selected from the group consisting of radioisotopes, fluorochromes, chromogens and enzymes.

7. The method of claim 1, wherein said solid carrier is easily removable from the hybridization mixture.

8. The kit of claim 3, wherein said solid carrier is easily removable from the hybridization mixture.

* * * * *